United States Patent [19]

Shum

[11] Patent Number: 5,026,938

[45] Date of Patent: Jun. 25, 1991

[54] PROCESS FOR UPGRADING LIGHT APPARATUS

[75] Inventor: Victor K. Shum, Naperville, Ill.

[73] Assignee: Amoco Corporation, Chicago, Ill.

[21] Appl. No.: 375,143

[22] Filed: Jun. 30, 1989

Related U.S. Application Data

[60] Continuation-in-part of Ser. No. 256,414, Oct. 12, 1988, Pat. No. 4,946,812, which is a division of Ser. No. 82,031, Aug. 5, 1987, Pat. No. 4,808,763.

[51] Int. Cl.$^5$ .............................................. C07C 2/00
[52] U.S. Cl. ..................................... 585/417; 585/419
[58] Field of Search ................................ 585/417, 419

[56] References Cited

U.S. PATENT DOCUMENTS

| | | | |
|---|---|---|---|
| 4,766,265 | 8/1988 | Desmond et al. | 585/417 |
| 4,891,463 | 1/1990 | Chu | 585/418 |

Primary Examiner—Curtis R. Davis
Attorney, Agent, or Firm—Ekkehard Schoettle; William H. Magidson; Ralph C. Medhurst

[57] ABSTRACT

The present invention relates to a process for producing aromatic compounds from a hydrocarbon gas containing $C_3$ through $C_5$ paraffinic hydrocarbons under conversion conditions in the presence of a catalyst comprising a gallosilicate molecular sieve, a platinum metal component, and a rhenium metal component.

15 Claims, No Drawings

PROCESS FOR UPGRADING LIGHT APPARATUS

This application is a continuation-in-part of U.S. Pat. application Ser. No. 256,414 filed on Oct. 12, 1988, now U.S. Pat. No. 4,946,812, which is a division of U.S. Pat. application Ser. No. 082,031 filed on Aug. 5, 1987 now U.S. Pat. No. 4,808,763.

Background of the Invention

The present invention is directed to a process for upgrading light paraffins such as propane, and butanes. Interest in upgrading these light paraffins has been growing due to recent and anticipated changes in refinery processing schemes which resulted and will result in a greater supply of such light paraffins. These changes include: the higher severity operation of the reforming process in order to maintain a high octane rating in the absence of or reduction of the lead content in gasoline; the lowering of reid vapor pressure (RVP) specifications; the increased use of oxygenates such as methyl tertiary butyl ether (MTBE) and ethanol resulting in the removal of butanes from the gasoline pool; the increased demand for jet fuel necessitating increased gas oil hydrocracking resulting in more light gas production, and the increase in operating temperatures in fluidized catalytic crackers resulting in more light gas production. Thus, there is great incentive to investigate means for converting these materials into more valuable liquids such as transportation fuels or chemical feedstocks.

The upgrading or conversion of light paraffinic gases and synthesis gas has previously been carried out in the presence of gallium-based or gallium-containing catalysts.

U.S. Pat. No. 4,543,347 (Heyward et al.) discloses a catalyst composition suitable for converting synthesis gas to hydrocarbons which is a mixture of zinc oxide and an oxide of at least one metal selected from gallium and iridium, an oxide of at least one additional metal collected from the elements of Group IB, II through V, VIB and VIII including the lanthanides and actinides and a porous crystalline tectometallic silicate.

U.S. Pat. No. 4,490,569 (Chu et al.) discloses a process for converting propane to aromatics over a zincgallium zeolite. This zeolite optionally may also contain palladium. More specifically, the catalyst composition used in the instant patent consists essentially of an aluminosilicate having gallium and zinc deposited thereon or an aluminosilicate in which cations have been exchanged with gallium and zinc ions wherein the aluminosilicate is selected from the group known as ZSM-5 type zeolites.

U.S. Pat. No. 4,585,641 (Barri et al.) discloses crystalline gallosilicates which may be impregnated, ion exchanged, admixed, supported or bound for catalyzing a reaction such as alkylation, dealkylation, dehydrocyclodimerization, transalkylation, isomerization, dehydrogenation, hydrogenation, cracking, hydrocracking, cyclization, polymerization, conversion of carbon monoxide and hydrogen mixtures through hydrocarbons and dehydration reaction. The metal compounds which may be used for ion exchange or impregnation may be compounds of any one of the groups of metals belonging to Groups IB, IIB, IIIA, IVA, VA, VIB, VIIB and VIII according to the Periodic Table. Specifically, preferred compounds include copper, silver, zinc, aluminum, gallium, indium, vanadium, lead, antimony, bismuth, chromium, molybdenum, tungsten, manganese, iron, cobalt, nickel, ruthenium, rhodium, palladium, iridium, platinum, radium, thorium and the rare earth metals. Patentees describe their gallosilicate as "Gallo Theta-1" in contradistinction to an MFI-type gallosilicate which has a substantially different X-ray diffraction pattern.

U.S. Pat. No. 4,350,835 (Chester et al.) relates to a catalytic process for converting gaseous feedstocks containing ethane to liquid aromatics by contacting the feed in the absence of air or oxygen under conversion conditions with a crystalline zeolite catalyst having incorporated therein a minor amount of gallium thereby converting the ethane to aromatics. The gallium is present in the catalyst as gallium oxide or as gallium ions if cations in the aluminosilicate have been exchanged with gallium ions. The patent further discloses that the original alkali metal of the zeolite, when it has been synthesized in the alkali metal form, may be converted to the hydrogen form or be replaced by ion exchange with other suitable metal cations of Groups I through VIII of the Periodic Table, including nickel, copper, zinc, palladium, calcium or rare earth metals.

European Patent Application 0 107 876 discloses a process for producing an aromatic hydrocarbon mixture from a feedstock containing more than 50 wt.% $C_2$ through $C_4$ paraffins. Specifically the process is carried out in the presence of crystalline gallium-silicate having a $SiO_2/Ga_2O_3$ molar ratio of 25 to 250 and a $Y_2O_3/GaO_3$ molar ratio lower than 1 where Y can be aluminum, iron, cobalt or chromium. The disclosure also teaches a two-step silicate treatment comprising a coke deposition and a coke burn-off with an oxygen-containing gas.

European Patent Application 0 107 875 similarly discloses a process for producing an aromatic hydrocarbon mixture from a feedstock comprising more than 50 wt.% of $C_2$ through $C_4$ paraffins. This process is carried out in the presence of a crystalline gallium-silicate, having a $SiO_2/Ga_2O_3$ molar ratio of 25 to 100 and a $Y_2O_2/Ga_2O_3$ molar ratio lower than 1 where Y can be aluminum, iron, cobalt or chromium.

U.S. Pat. No. 4,629,818 (Burress) discloses an aromatization catalyst that contains gallium and thorium incorporated with a ZSM-5 or ZSM-11 component.

Similarly, U.S. Pat. No. 4,350,835 (Chester et al.) discloses a catalyst suitable for converting ethane to benzene, toluene, and xylene with a catalyst comprising gallium and a zeolite such as ZSM-5, ZSM-11, ZSM-12, ZSM-35, and ZSM-38. Along the same vein, U.S. Pat. No. 4,766,264 (Bennett et al.) discloses a gallium-loaded zeolite aromatization catalyst.

Light paraffinic gases have also been upgraded to liquid aromatics in the presence of crystalline aluminosilicate zeolite catalysts having incorporated therein a minor amount of a metal selected from Groups VIII, IIB, and IB of the Periodic Table. For instance, U.S. Pat. No. 4,120,910 (Chu) discloses copper-zinc-HZSM-5, platinum-HZSM-5, copper-HZSM-5, and zinc-HZSM-5 catalysts suitable for upgrading a gaseous paraffinic hydrocarbon feed to aromatic compounds.

U.S. Pat. No. 4,704,494 (Inui) discloses a process for the conversion of low molecular paraffin hydrocarbons to aromatic hydrocarbons in the presence of metallosilicates wherein the metal is Al, Ga, Ti, Zr, Ge, La, Mn, Cr, Sc, V, Fe, W, Mo, or Ni.

International Application No. PCT/GB84/00109 (International Publication Number: WO84/03879) (Barlow) discloses an aromatization process utilizing a catalyst having a Group VIII metal in combination with a galloaluminosilicate.

It is also known to employ a rhenium component and a platinum component in reforming and light paraffin dehydrocyclization catalysts.

U.S. Pat. No. 4,416,806 (Bernard et al.) discloses a paraffin dehydrocyclization catalyst that contains a zeolitic crystalline aluminosilicate such as faujasite X, faujasite Y, zeolite L, zeolite omega, and zeolite ZSM-4. This catalyst also contains a rhenium component incorporated in the form of a carbonyl, a sulfur component and a platinum component.

U.S. Pat. No. 4,105,541 (Plank et al.) broadly discloses an aromatization catalyst containing ZSM-38 that can have its original cations replaced by ion exchange with a mixture of cations selected from the group consisting of hydrogen, rare earth metals and metals from Groups IIA, IIIA, IVA, IB, IIB, IIIB, IVB, VIB, and VIII.

U.S. Pat. No. 4,613,716 (McNiff) discloses a process for aromatizing ethane and/or ethylene with a catalyst containing an aluminosilicate loaded with gallium compounds or ions and a compound of a metal from Group VIIB or Group VIII specifically rhenium or iridium.

Finally, U.S. Pat. No. 4,766,265 (Desmond) teaches a process for the conversion of ethane to liquid aromatic compounds using a catalyst containing a gallium impregnated molecular sieve with both a rhenium component and a metal selected from the group consisting of nickel, palladium, platinum, rhodium and iridium. The molecular sieve can be an alumino-, gallo-, or borosilicate. Silica is the preferred binder material for the catalytic composite. The '265 process is directed to handling ethane-rich, ethane feedstocks ranging from 100% ethane to a feedstock containing only minor amounts of ethane in a feedstock predominantly of hydrogen, methanol, and relatively minor amounts of $C_2$-$C_5$ and $C_3$-$C_5$ paraffins.

In contrast to the '265 process, the process of the present invention, is directed to the conversion of a hydrocarbon gas rich in $C_3$ through $C_5$ light paraffins, preferably a feedstock rich in either $C_3$ and/or $C_4$. Further, the process of the present invention does not require the ion exchange or impregnation of the molecular sieve contained in the catalyst with a gallium compound.

It has now been discovered that $C_3$ through $C_5$ light paraffins can most effectively be upgraded by the catalytic process of the present invention minimizing methane and ethane production while simultaneously maximizing benzene, toluene and xylene production.

SUMMARY OF THE INVENTION

Briefly stated, in a broad aspect, this invention relates to a process for producing aromatic compounds from a hydrocarbon gas rich in paraffinic hydrocarbons ranging from $C_3$ to $C_5$ under conversion conditions in the presence of a catalyst comprising a gallosilicate molecular sieve, a platinum metal component, and a rhenium metal component.

DETAILED DESCRIPTION OF THE INVENTION

The present invention deals with the conversion of a hydrocarbon gas rich in paraffinic hydrocarbons ranging from $C_3$ to $C_5$ to aromatics. A particularly suitable feedstock for use in the present invention contains $C_3$ and/or $C_4$ paraffins. The feedstock suitable for use in the present invention preferably contains less than 10% ethane and most preferably a relatively minor amount of ethane such as less than 5%. Minor amounts of methane can also be present. In addition to the above-mentioned paraffins, the feedstock may contain other light gases such as propylene, butene, isobutene, butadiene, and paraffins and olefins with five or more carbon atoms per molecule. These feedstocks are generally available from several sources in a refinery as elucidated above.

The process of the invention provides for the direct conversion of the light paraffinic gases to valuable aromatic hydrocarbons such as benzene, toluene, and xylenes. These aromatics can be used as an additive component to increase the octane number of gasoline or as raw materials in the petrochemical industry.

The process of the invention selectively provides for a high yield of benzene, toluene, and xylenes in the $C_4$+product fraction while minimizing the yield of light $C_1$ and $C_2$ gases and $C_9$+ aromatic compounds in the product fraction.

Broadly, the catalyst employed according to the process of the present invention comprises a gallosilicate molecular sieve component and a platinum metal component. The gallosilicate can be prepared using conventional methods known to those skilled in the art. A suitable method is disclosed in European Patent Application 01 107 875 which is incorporated herein by reference.

In another method the gallosilicate crystalline molecular sieves of this invention are characterized by the representative X-ray pattern listed in Table I below and by the composition formula:

$$0.9 \pm 0.2 \, M_{2/n}O : Ga_2O_3 : ySiO_2 : zH_2O$$

wherein M is at least one cation, n is the valence of the cation, y is between 4 and about 600, and z is between 0 and about 160. It is believed that the small gallium content of the sieves is at least in part incorporated in the crystalline lattice. Various attempts to remove the gallium from the gallosilicate sieves by exhaustive exchange with sodium, ammonium, and hydrogen ions were unsuccessful and therefore, the gallium content is considered nonexchangeable in the instant sieves prepared according to the present method.

TABLE I

| d-Spacing Å (1) | Assigned Strength (2) | d-Spacing Å (1) | Assigned Strength (2) |
|---|---|---|---|
| 11.10 ± 0.20 | VS | 3.84 ± 0.10 | MS |
| 9.96 ± 0.20 | MS | 3.71 ± 0.10 | M |
| 6.34 ± 0.20 | W | 3.64 ± 0.10 | W |
| 5.97 ± 0.20 | W | 2.98 ± 0.10 | VW |
| 5.55 ± 0.20 | W | | |
| 4.25 ± 0.10 | VW | | |

(1) Copper K alpha radiation
(2) VW = very weak; W = weak; M = medium; MS = medium strong; VS = very strong A gallosilicate molecular sieve useful in this invention can be prepared by crystallizing an aqueous mixture, at a controlled pH, of a base, a gallium ion-affording material, an oxide of silicon, and an organic template compound.

Typically, the molar ratios of the various reactants can be varied to produce the crystalline gallosilicates of this invention. Specifically, the molar ratios of the initial reactant concentrations are indicated below:

TABLE II

|  | Broad | Preferred | Most Preferred |
| --- | --- | --- | --- |
| $SiO_2/Ga_2O_3$ | 4–200 | 10–150 | 20–100 |
| Organic base/$SiO_2$ | 0.5–5 | 0.05–1 | 0.1–0.5 |
| $H_2O/SiO_2$ | 5–80 | 10–50 | 20–40 |
| Template/$SiO_2$ | 0–1 | 0.01–0.2 | 0.02–0.1 |

By regulation of the quantity of gallium (represented as $Ga_2O_3$) in the reaction mixture, it is possible to vary the $SiO_2/Ga_2O_3$ molar ratio in the final product. In general, it is desirable to have the gallium content of the gallosilicate sieve of this invention between about 0.1 and about 8 percent by weight of gallium. More preferably, the amount of gallium should be between about 0.2 and about 6 weight percent gallium and, most preferably, between about 0.3 and about 4 weight percent of gallium. Too much gallium in the reaction mixture appears to reduce the sieve crystallinity which reduces the catalytic usefulness of the sieve.

More specifically, a material useful in the present invention is prepared by mixing a base, a gallium ion-affording substance, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.5 and 11.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water insoluble gallium compounds such as the oxide can be used as well.

Cations useful in the formation of the gallosilicate sieves include the sodium ion and the ammonium ion. The sieves also can be prepared directly in the hydrogen form with an organic base such as ethylenediamine.

The acidity of the gallosilicate sieves of this invention is high as measured by the Hammett $H_o$ function which lies in the neighborhood of about −3 to about −6.

Organic templates useful in preparing the crystalline gallosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline gallosilicate molecular sieve can be prepared by crystallizing a mixture of sources for an oxide of silicon, an oxide of gallium, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. The molar ratio of base to silicon oxide should be about above about 0.5, typically below about 5, preferably between about 0.05 and about 1.0 and most preferably between about 0.1 and about 0.5. The molar ratio of aklylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 25 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 hours. The gallosilicate sieves thus made generally have a surface area greater than about 300 sq. meters per gram as measured by the BET procedure.

Although not required, it is preferred to employ the above-described gallosilicate molecular sieve combined, dispersed or otherwise intimately admixed in a matrix of at least one non-molecular sieve, porous refractory inorganic oxide matrix component, as the use of such a matrix component facilitates the provision of the ultimate catalyst in a shape or form well suited for process use. Useful matrix components include alumina, silica, silica-alumina, zirconia, titania, etc., and various combinations thereof. In a specific embodiment of the present invention silica is the most preferred inorganic refractory oxide. The matrix components also can contain various adjuvants such as phosphorus oxides, boron oxides, and/or halogens such as fluorine or chlorine. Usefully, the molecular sieve-matrix dispersion contains about 1 to 99 wt.% of a sieve component, preferably 20 to about 90 wt.% and most preferably 30 to 80 wt.% of a sieve component based upon the sieve-matrix dispersion weight.

Methods for dispersing molecular sieve materials within a matrix component are well-known to persons skilled in the art and applicable with respect to the gallosilicate molecular sieve materials employed according to the present invention. A method is to blend the molecular sieve component, preferably in finely-divided form, in a sol, hydrosol or hydrogel of an inorganic oxide, and then add a gelling medium such as ammonium hydroxide to the blend, with stirring, to produce a gel. The resulting gel can be dried, shaped if desired, and calcined. Drying preferably is conducted in air at a temperature of about 80° to about 350° F. (about 27° to about 177° C.) for a period of several seconds to several hours. Calcination preferably is conducted by heating in air at about 800° to about 1,200° F. (about 427° to about 649° C.) for a period of time ranging from about ½ to about 16 hours.

Another suitable method for preparing a dispersion of the molecular sieve component in a porous refractory oxide matrix component is to dry blend particles of each, preferably in finely-divided form, and then shape the dispersion if desired.

Alternatively, in another method, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° to about 150° C. and then calcined at between about 350° and about 700° C., more preferably between about 400° to about 650° C.

Silica-supported catalyst compositions can be made by dry mixing the gallosilicate sieve with a silica source such as Cab-O-Sil, adding water and stirring. The resulting solid is then dried below about 200° C. and finally calcined between about 350° C. and 700° C.

The platinum metal component of the catalyst employed according to the present invention can be present in elemental form, as oxides, as nitrates, as chlorides or other inorganic salts, or as combinations thereof. While other Group VIII metals can be employed in the present invention, platinum is preferred because it is relatively inactive for hydrogenolysis which would result in undesirable increased yields of $C_1$ and $C_2$.

The platinum metal component content preferably ranges from about 0.01 to about 10 wt.%, calculated as a zero valent metal and being based on the total weight of the catalytic final composite, with about 0.01 to about 5 wt.% being more preferred, with a range of 0.05 to 1.0 wt.% being most preferred. Higher levels of platinum can be employed if desired, though the degree of improvement resulting therefrom typically is insufficient to justify the added cost of the metal.

The rhenium metal component content employed according to the present invention can be present in elemental form, as oxides, as nitrates, as chlorides, or other inorganic salts, or combinations thereof.

The rhenium metal component content preferably ranges from about 0.01 wt.% to about 10 wt.% calculated as a zero valent metal and being based on the total weight of the catalytic final composite, with a range of about 0.01 wt.% to about 5 wt.% being more preferred, with a range of about 0.05 wt.% to about 2 wt.% being most preferred.

The platinum metal and rhenium metal components of the catalyst employed according to this invention can be associated with the sieve component by impregnation of the sieve component, or the sieve component can be dispersed in a porous refractory inorganic oxide matrix, with one or more solutions of compounds of the platinum and rhenium, metal components which components are convertible to oxides on calcination. It also is contemplated, however, to impregnate a porous refractory inorganic oxide matrix component with such solutions of the platinum metal and rhenium metal components and then blend the sieve component with the resulting impregnation product. Accordingly, the present invention contemplates the use of catalysts in which the platinum metal and rhenium metal components are deposed on the sieve component, on a sieve matrix component dispersion or on the matrix component of a sieve matrix component. The order of incorporation of the metal components with the sieve component or sieve component and refractory inorganic oxide matrix component is not material.

The mechanics of impregnating the sieve component, matrix component or matrix composite with solutions of compounds convertible to metal oxides on calcination are well-known to persons skilled in the art and generally involve forming solutions of appropriate compounds in suitable solvents, preferably water, and then contacting the sieve matrix component or sieve matrix dispersion with an amount or amounts of solution or solutions sufficient to deposit appropriate amounts of metal or metal salts onto the sieve or sieve matrix dispersion. Useful metal compounds convertible to oxides are well-known to persons skilled in the art and include various ammonium salts as well as metal acetates, nitrates, anhydrides, etc.

In another embodiment of the present invention the catalyst of the present invention also contains chloride. The addition of chloride to the catalyst serves to increase the conversion and selectivity of the process of the invention to aromatics. A convenient method of adding the chloride is to include a predetermined volume of a solution containing a predetermined concentration of hydrochloric acid in the impregnating solution used to incorporate the platinum metal component with the catalyst.

Alternatively, the chloride can also be added during the impregnation of the metal salt if the metal salt contains chloride, such as hydrogen hexachloroplatinate ($H_2PtCl_6 \cdot 6H_2O$). If the chloride content in the chloride-containing metal salt is not sufficiently high, additional chloride can be added by the addition of hydrochloric acid to the impregnating solution.

In the instant embodiment of the invention, the catalyst broadly contains 0.1 to 10 wt.% chloride, preferably 0.5 to 5 wt.% chloride and most preferably 0.5 to 1.5 wt.% chloride based on the final catalyst weight.

Also contemplated within the purview of the present invention, chloride can be incorporated into the catalyst by the addition of chloride-containing compounds to the feed stream such as carbon tetrachloride, hydrochloric acid, in amounts such that the final catalyst contains the above prescribed amount of chloride.

The above-described catalysts can be employed in any suitable form such as spheres, extrudates, pellets, or C-shaped or cloverleaf-shaped particles.

The process of the present invention is carried out under suitable operating conditions set out below in Table III under which the feed is contacted with the above-described catalyst. It is also contemplated that a portion of the unconverted effluent stream can be recycled to the feed after separation from the aromatic products.

TABLE III

|  | Broad | Preferred | Most Preferred |
| --- | --- | --- | --- |
| Conditions |  |  |  |
| Temperature, °F. | 700-1400 | 800-1200 | 850-1150 |
| Total Pressure, psig | 0-500 | 0-300 | 0-100 |
| WHSV, $h^{-1}$ | 0.1-100 | 0.1-40 | 0.1-20 |

The present invention is described in further detail in connection with the following examples, it being understood that the same are for purposes of illustration only and not limitation.

EXAMPLE I

The present example serves to demonstrate the process of the present invention. A gallosilicate molecular sieve was first impregnated to incipient wetness with an aqueous solution of ammonium perrhenate with a concentration calculated to yield 1.0 wt% elemental Re. The dried Re-loaded gallosilicate was then impregnated to incipient wetness with an aqueous solution of tetraamine platinum nitrate having a concentration calculated to yield 1.0 wt% elemental Pt. The dried Pt- and Re-loaded gallosilicate was then uniformly mixed with Catalpal alumina (alpha alumina monohydrate), then slurried with water to form a paste, and finally extruded to yield 1/16" extrudate. The extrudate was dried and calcined. The amount of Catalpal alumina used was calculated to yield 60 wt% molecular sieve and 40 wt% alumina in the dried extrudate. The elemental metal loadings were 0.6 wt% Pt and 0.6 wt% Re with respect to the final extrudate catalyst. The 1/16" extrudate was then passed through a set of sieves to obtain 10-20 mesh particles for testing.

This catalyst was then tested for n-butane conversion in accordance with the present invention in a conventional tubular fixed-bed once-through reactor, which had not been exposed to sulfur. The catalyst was reduced in the presence of hydrogen at 900° F. prior to charging the n-butane. The feed was 100% n-butane. Gas and liquid products were separated and analyzed by gas chromatography. Process parameters and results are summarized in Table IV below.

EXAMPLE 2

The platinum/rhenium/gallosilicate catalyst prepared as described in Example 1 was sulfided in situ after reduction with a hydrogen stream containing 500 ppm hydrogen sulfide at 900° F. until hydrogen sulfide breakthrough. Weakly-adsorbed sulfur was then purged with hydrogen at 900° F. This sulfided catalyst was then tested for n-butane conversion as in Example 1. Process parameters and results are summarized in Table V below.

EXAMPLE 3

A platinum/gallosilicate extrudate catalyst was prepared as described in Example 1 except that the rhenium component was omitted not in accordance with the present invention. The extrudate contained 60 wt% molecular sieve and 40 wt% alumina binder. The elemental Pt loading was 0.6 wt% with respect to the final catalytic composite. As in Example 1, 10-20 mesh particles were obtained for catalytic testing. Process parameters and results are summarized in Table VI below.

EXAMPLE 4

In the present Example a platinum/gallosilicate extrudate catalyst was prepared. The present catalyst is the same as the catalyst in Example 1 except that the rhenium compound was omitted. The extrudate contained 60 wt% molecular sieve and 40 wt% alumina binder. The elemental Pt loading was higher at 1.0 wt% with respect to the final extrudate. As in Example 1, 10-20 mesh particles were obtained for the testing. The process parameters and results are summarized in Table VII below:

TABLE IV

| Pt/Re/Gallosilicate Extrudate Catalyst (0.6% Pt-0.6% Re) | |
| --- | --- |
| Temperature: 900° F. | |
| Pressure: 1 atm | |
| WHSV: 2 g butane/g catalyst-hour | |
| Time on stream: 1.2 h | |
| Conversion of n-butane, C % | 90.0 |
| Selectivity, C % | |
| Methane | 4.6 |
| Ethane | 17.8 |
| Ethylene | 0.4 |
| Propane | 11.9 |
| Propylene | 3.6 |
| Isobutane | 2.5 |
| Butylenes | 10.2 |
| $C_5+$ PON* | 0.3 |
| Aromatics | 48.7 |
| Aromatics distribution, wt % | |
| Benzene | 21.2 |
| Toluene | 36.4 |
| Xylenes | 35.3 |
| $C_9$ | 2.3 |
| $C_{10}$ | 1.5 |
| $C_{11}+$ | 3.3 |
| Selectivity to $H_2$, mol % | 31.7 |
| (mole of hydrogen produced per mole of hydrogen in the converted butane) | |
| Carbon mass balance, % | 93.6 |

*PON = Paraffins, Olefins, Naphthenes

TABLE V

| (S) Pt/Re/Gallosilicate Extrudate Catalyst (0.6% Pt-0.6% Re) | |
| --- | --- |
| Temperature: 900° F. | |
| Pressure: 1 atm | |
| WHSV: 2 g butane/g catalyst-hour | |
| Time on stream: 2.1 h | |
| Conversion of n-butane, C % | 81.5 |
| Selectivity, C % | |
| Methane | 4.1 |
| Ethane | 12.2 |
| Ethylene | 1.0 |
| Propane | 10.6 |
| Propylene | 5.6 |
| Isobutane | 3.4 |
| Butylenes | 17.4 |
| $C_5+$ PON* | 1.7 |
| Aromatics | 44.0 |
| Aromatics distribution, wt % | |
| Benzene | 15.2 |
| Toluene | 28.5 |

TABLE V-continued

| (S) Pt/Re/Gallosilicate Extrudate Catalyst (0.6% Pt-0.6% Re) | |
|---|---|
| Xylenes | 45.2 |
| $C_9$ | 4.0 |
| $C_{10}$ | 3.3 |
| $C_{11}+$ | 3.8 |
| Selectivity to $H_2$, mol % (mole of hydrogen produced per mole of hydrogen in the converted butane) | 25.7 |
| Carbon mass balance, % | 95.4 |

*PON = Paraffins, Olefins, Naphthenes

TABLE VI

| Pt/Gallosilicate Extrudate Catalyst (0.6% Pt) | |
|---|---|
| Temperature: 900° F. | |
| Pressure: 1 atm | |
| WHSV: 2 g butane/g catalyst-hour | |
| Time on stream: 2.0 h | |
| Conversion of n-butane, C % | 90.0 |
| Selectivity, C % | |
| Methane | 4.6 |
| Ethane | 20.9 |
| Ethylene | 0.1 |
| Propane | 19.7 |
| Propylene | 0.8 |
| Isobutane | 3.1 |
| Butylenes | 3.5 |
| $C_5+$ PON | 0.4 |
| Aromatics | 46.9 |
| Aromatics distribution, wt % | |
| Benzene | 20.2 |
| Toluene | 33.3 |
| Xylenes | 37.0 |
| $C_9$ | 3.2 |
| $C_{10}$ | 2.8 |
| $C_{11}+$ | 3.5 |
| Selectivity to $H_2$, mol % (mole of hydrogen produced per mole of hydrogen in the converted butane) | 23.8 |
| Carbon mass balance, % | 95.4 |

*PON = Paraffins, Olefins, Naphthenes

TABLE VII

| Pt/Gallosilicate Extrudate Catalyst (1.0% Pt) | |
|---|---|
| Temperature: 900° F. | |
| Pressure: 1 atm | |
| WHSV: 2 g butane/g catalyst-hour | |
| Time on stream: 2.0 h | |
| Conversion of n-butane, C % | 87.1 |
| Selectivity, C % | |
| Methane | 4.5 |
| Ethane | 18.9 |
| Ethylene | 0.2 |
| Propane | 17.8 |
| Propylene | 2.1 |
| Isobutane | 3.3 |
| Butylenes | 8.5 |
| $C_5+$ PON | 0.6 |
| Aromatics | 44.1 |
| Aromatics distribution, wt % | |
| Benzene | 17.8 |
| Toluene | 29.8 |
| Xylenes | 43.2 |
| $C_9$ | 4.1 |
| $C_{10}$ | 2.7 |
| $C_{11}+$ | 2.4 |
| Selectivity to $H_2$, mol % (mole of hydrogen produced per mole of hydrogen in the converted butane) | 26.3 |
| Carbon mass balance, % | 96.0 |

*PON = Paraffins, Olefins, Naphthenes

DISCUSSION OF RESULTS

A comparison of Tables IV and V show that the sulfided platinum/rhenium/gallosilicate (Table V) is not superior to the unsulfided invention Example 1 catalyst (Table IV) in both activity, selectivity to aromatics and selectivity to hydrogen. Thus, Pt/Re/gallosilicate does not require sulfidation for good catalytic performance.

This is in contrast to a prior art naphtha reforming catalyst, namely, a platinum/rhenium/alumina catalyst which requires sulfidation to achieve acceptable performance of the catalyst as demonstrated in V. K. Shum et al., J. Catal. 96, 371–380 (1985).

A comparison of Table IV with either Table VI or Table VII shows that the invention Pt/Re/gallosilicate is more selective towards relatively high-valued products than the prior art Pt/gallosilicate at either a comparable platinum metal loading or comparable total metal loading. These highly-valued products include aromatics (used as high-octane gasoline blending stock or chemical feedstocks), butylenes and isobutane (both used for alkylation to produce high-octane isoparaffinic gasoline blending stock), and hydrogen (used for refinery streams hydroprocessing). Methane, ethane and propane are relatively low-valued byproducts.

EXAMPLE 5

A platinum/rhenium/gallosilicate molecular sieve catalyst, in accordance with the present invention containing 0.45 wt% Pt and 0.45 wt% Re was mechanically mixed with Cab-O-Sil EH-5 grade silica at a ratio of 60 wt% sieve to 40% wt% silica. Water was added to the mixed powder to form a slurry, which was then vigorously agitated in a high-speed blender. The resulting uniformly-mixed slurry was then dried in an oven to obtain a cake, which was then calcined in air at elevated temperature. The cake was then crushed and passed through a sieve to obtain 10-20 mesh particles for testing.

This silica-containing catalyst was then tested for n-butane conversion in accordance with the process of the present invention in a conventional tubular fixed-bed reactor. The feed was 100% n-butane. Gas and liquid products were separated and analyzed by gas chromatography. Process parameters and results are set out in Table VIII below.

EXAMPLE 6

The platinum/rhenium/gallosilicate catalyst described in Example 1 containing 0.45 wt% Pt and 0.45 wt% Re was mechanically mixed with Catalpal alumina at a ratio of 60 wt% sieve and 40 wt% alumina. The mixed powder was slurried with water in a high-speed blender. The slurry was dried and calcined to form a cake which was crushed and passed through a sieve to obtain 10–20 mesh particles.

This alumina-containing catalyst was then tested for n-butane conversion in accordance with the process of the present invention as set out in Example 5. Process parameters and results are set out in Table IX below.

EXAMPLE 7

The platinum/rhenium/gallosilicate catalyst described in Example 1 containing 0.45 wt% Pt and 0.45 wt% Re was pressed into tablets without any matrix (binder). The tablets were crushed and passed through a sieve to obtain 10-20 mesh particles for catalytic testing.

This catalyst-containing no refractory inorganic oxide binder catalyst was also tested for n-butane conversion described in Example 5 in accordance with the process of the present invention. Process parameters and results are presented in Table X below.

TABLE VIII

| Binder type | Silica |
|---|---|
| Temperature, °F. | 900 |
| Pressure, atm | 1 |
| Time on stream, h | 2 |
| WHSV (based on catalyst), /h | 2.0 |
| WHSV (based on molecular sieve), /h | 3.3 |
| Molecular sieve loading, wt % | 60 |
| Conversion of n-butane, C-wt % | 78.1 |
| Selectivity to aromatics, C-wt % | 37.2 |
| Carbon mass balance, % | 96.4 |

TABLE IX

| Binder type | Alumina |
|---|---|
| Temperature, °F. | 900 |
| Pressure, atm | 1 |
| Time on stream, h | 2 |
| WHSV (based on catalyst), /h | 2.0 |
| WHSV (based on molecular sieve), /h | 3.3 |
| Molecular sieve loading, wt % | 60 |
| Conversion of n-butane, C-wt % | 44.9 |
| Selectivity to aromatics, C-wt % | 34.0 |
| Carbon mass balance, % | 97.3 |

TABLE X

| Binder type | NA |
|---|---|
| Temperature, °F. | 900 |
| Pressure, atm | 1 |
| Time on stream, h | 2 |
| WHSV (based on catalyst), /h | 2.0 |
| WHSV (based on molecular sieve), /h | 2.0 |
| Molecular sieve loading, wt % | 100 |
| Conversion of n-butane, C-wt % | 76.0 |
| Selectivity to aromatics, C-wt % | 30.7 |
| Carbon mass balance, % | 96.6 |

Discussion of Results

A comparison of Tables VIII and X shows that when the silica-containing catalyst (60 wt% sieve) and all-sieve catalyst were tested under the same weight hourly space velocity (WHSV) based on the as-charged catalyst with other process parameters held constant, the silica-containing catalyst was at least as active as the "all-sieve" catalyst. The silica-containing catalyst was also more selective towards aromatics production. These are surprising results since the silica-containing catalyst contains 40 wt% less molecular sieve, and silica by itself is considered to be catalytically inert for the reactions involved in the process of the present invention.

A comparison of Tables IX and X shows that when the alumina-containing catalyst (60 wt% sieve) and the "all-sieve" catalyst were tested under the same WHSV based on the as-charged catalyst with other process parameters held constant, the alumina-containing catalyst was about 60% as active as the all-sieve catalyst. This was expected, since the alumina-bound catalyst contains only 60 wt% of the molecular sieve contained in the "all sieve" catalyst.

Thus, as shown in Tables VIII through X, all of the catalysts used in accordance with the process of the present invention possess light paraffin aromatization activity. The catalyst in Example 5 possesses enhanced light paraffin aromatization activity despite containing less sieve. Thus, in a preferred embodiment of the present invention the catalyst contains silica as the refractory inorganic oxide as the binder of matrix material. Thus, the use of silica permits the preparation of a catalyst having greater mechanical strength and less cost due to the decreased sieve content.

What is claimed is:

1. A process for converting a gaseous hydrocarbon feed containing $C_3$ through $C_5$ paraffinic hydrocarbons to aromatic hydrocarbons which comprises contacting the feed under conversion conditions with a catalyst composition comprising a molecular sieve consisting essentially of a gallosilicate molecular sieve, a platinum metal component, and a rhenium metal component.

2. The process of claim 1 wherein the gaseous feed comprises $C_3$ and $C_4$ paraffins.

3. The process of claim 2 wherein the gaseous feed comprises butane.

4. The process of claim 1 wherein the gallosilicate molecular sieve is dispersed within a non-molecular sieve containing porous refractory inorganic oxide matrix component.

5. The process of claim 1 wherein the platinum metal component is present in an amount ranging from about 0.01 to about 10 wt.% calculated as the zero valent metal and based on the total weight of the composition.

6. The process of claim 1 wherein the rhenium metal component is present in an amount ranging from about 0.01 to about 10 wt.% calculated as the zero valent metal and based on the total weight of the composition.

7. The process of claim 4 wherein the gallosilicate molecular sieve is present in the dispersion such that the weight of the gallosilicate ranges from about 20 to 90 wt.% based on the weight of the gallosilicate - refractory inorganic oxide dispersion.

8. The process of claim 4 wherein the gallosilicate molecular sieve is present in the dispersion such that the weight of the gallosilicate ranges from about 30 to 80 wt.% based on the weight of the gallosilicate - refractory inorganic oxide dispersion.

9. The process of claim 8 wherein the refractory inorganic oxide component is selected from a group consisting of silica, silica-alumina, and alumina.

10. The process of claim 9 wherein the refractory inorganic oxide component is silica.

11. The process of claim 1 herein the platinum metal component is present in an amount ranging from about 0.01 to about 5 wt.% calculated as the zero valent metal and based on the total weight of the composition.

12. The process of claim 1 wherein the rhenium component is present in an amount ranging from about 0.01 to about 5 wt.% calculated as the zero valent metal and based on the total weight of the composition.

13. The process of claim 1 wherein the platinum metal component is present in an amount ranging from about 0.05 to about 1.0 wt.% calculated and the rhenium metal component is present in an amount ranging from about 0.05 to about 2 wt.% both as the zero valent metal and based on the total weight of the final composition.

14. The process of claim 8 wherein the platinum metal component is present in an amount ranging from about 0.05 to about 1.0 wt.% and the rhenium metal component is present in an amount ranging from about .05 to about 2 wt.% both calculated as the zero valent metal and based on the total weight of the final composition.

15. The process of claim 20 wherein the platinum metal component is present in an amount ranging from about 0.05 to about 1.0 wt.% and the rhenium metal component is present in an amount ranging from about .05 to about 2 wt.% both calculated as the zero valent metal and based on the total weight of the final composition.

* * * * *